(12) United States Patent
Soon-Shiong

(10) Patent No.: US 11,554,167 B2
(45) Date of Patent: Jan. 17, 2023

(54) BACILLUS CALMETTE-GUERIN (BCG) AND ANTIGEN PRESENTING CELLS FOR TREATMENT OF BLADDER CANCER

(71) Applicant: NantCell, Inc., Culver City, CA (US)

(72) Inventor: Patrick Soon-Shiong, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

(21) Appl. No.: 17/747,253

(22) Filed: May 18, 2022

(65) Prior Publication Data

US 2022/0288182 A1 Sep. 15, 2022

Related U.S. Application Data

(62) Division of application No. 16/932,331, filed on Jul. 17, 2020, now Pat. No. 11,364,291.

(60) Provisional application No. 62/875,663, filed on Jul. 18, 2019.

(51) Int. Cl.
*A61K 39/04* (2006.01)
*A61K 35/15* (2015.01)
*A61K 39/00* (2006.01)

(52) U.S. Cl.
CPC .............. *A61K 39/04* (2013.01); *A61K 35/15* (2013.01); *A61K 2039/585* (2013.01)

(58) Field of Classification Search
None
See application file for complete search history.

(56) References Cited

U.S. PATENT DOCUMENTS

2014/0134128 A1* 5/2014 Wong ................. A61P 37/04
424/85.2

FOREIGN PATENT DOCUMENTS

WO WO-2018112360 A1 * 6/2018

OTHER PUBLICATIONS

Kumar et al. Biol Open. Jun. 15, 2018; 7(6): bio032045 (8 pages).*
Gomes-Giacoia et al. PloS ONE96):e96705 (11 pages) 2014.*
U.S. Appl. No. 16/932,331, filed Jul. 17, 2020, Soon-Shiong.
Sylvester, "Bacillus Calmette-Guérin treatment of non-muscle invasive bladder cancer," International Journal of Urology, Feb. 2011, vol. 18(2), pp. 113-120.
Biot, et al., "Preexisting BCG-Specific T Cells Improve Intravesical Immunotherapy for Bladder Cancer," Science Translational Medicine, Jun. 6, 2012, vol. 4(137), p. 137ra72, abstract only, 1 page.
Romee et al. Blood. 131 (23): 2515-2527, 2018.
Anguille et al. Journal of Translational Medicine, 7(109): 1-16, 2009.
van Willigen et al. Front. Immunol. vol. 9, 2265: 1-13, 2018.
Morton et al. Ann Surg 180(4):635-641, 1974.
Morales. The Canadian Journal of Urology, 24(3):8788-8793, 2017.
Nishiyama et al. Clincal Cancer Research, 7:23-31, 2001.
Beatty. BJU Int. Dec. 2004; 94(9):1377-83, 2004.
Anguille et al. Human Vaccines and Immunotherapeutics 9:9, 1956-1961, 2013.
Bol et al. Oncoimmunology, 5:1, pp. 1-9, 2016.
Official Action for U.S. Appl. No. 16/932,331, dated Nov. 16, 2021 7 pages, Restriction Requirement.
Official Action for U.S. Appl. No. 16/932,331, dated Jan. 27, 2022 19 pages.
Notice of Allowance for U.S. Appl. No. 16/932,331, dated Apr. 27, 2022 10 pages.

* cited by examiner

*Primary Examiner* — Oluwatosin A Ogunbiyi
(74) *Attorney, Agent, or Firm* — Sheridan Ross P.C.

(57) ABSTRACT

Combination therapeutics for the treatment of cancer include the use of immune effector cells, IL-15 based superagonists and one or more immunotherapeutic agents such as *Bacillus Calmette-Guerin* (BCG).

9 Claims, No Drawings

Specification includes a Sequence Listing.

ered with BCG.

BACILLUS CALMETTE-GUERIN (BCG) AND ANTIGEN PRESENTING CELLS FOR TREATMENT OF BLADDER CANCER

CROSS-REFERENCE TO RELATED APPLICATIONS

This application is a divisional of U.S. patent application Ser. No. 16/932,331, filed Jul. 17, 2020, now U.S. Pat. No. 11,364,291, which claims the benefit of priority under 35 U.S.C. § 119(e) to U.S. Provisional Patent Application No. 62/875,663, filed Jul. 18, 2019. The entire disclosures of each of which is incorporated herein by reference.

REFERENCE TO A SEQUENCE LISTING

This application contains a Sequence Listing submitted electronically as a text file by EFS-Web. The text file, named "8774-35-Seq_Listing_ST25", has a size in bytes of 10,000 B, and was recorded on 31 Mar. 2022. The information contained in the text file is incorporated herein by reference in its entirety pursuant to 37 CFR § 1.52(e)(5).

FIELD OF THE INVENTION

Embodiments of the invention are directed to treatment of bladder cancer using compositions that induce an immune response to bladder cancer cells. In particular, the compositions include antigen presenting cells, isolated from subjects treated with *Bacillus* Calmette-Guerin (BCG) and cultured with IL-15 based superagonists.

BACKGROUND

Urothelial carcinoma is the most common bladder cancer (BC) with an incidence of approximately 90%. At diagnosis two-third of urothelial carcinomas are non-muscle invasive and one-third are muscle invasive. Non-muscle invasive bladder cancer (NMIBC) is characterized by a high risk of recurrence (30-85% depending on stage and grade) after transurethral resection of the bladder tumor (TURBT). Moreover, up to 17% of all NMIBC will eventually progress to muscle invasive bladder cancer (MIBC). Non-muscle invasive bladder cancer (NMIBC) begins and stays in the cells lining the bladder without growing into the deeper main muscle layer of the bladder, and accounts for the majority (70-80%) of patients diagnosed with bladder cancer (stages Ta, T1, or CIS). Approximately 30% of patients present with muscle-invasive disease (stages T2-T4). Bladder cancer has the highest recurrence rate of any malignancy.

A significant limitation of current *Bacillus* Calmette-Guerin (BCG) treatment is the lack of response in a substantial number of patients. For example, depending on the endpoint studied, up to 50% of patients fail to respond and show progression of the cancer to muscle invasive disease. Additionally, approximately one-third of patients that initially respond to therapy will show tumor recurrence (Sylvester, R. J., *Int J Urol.*, February; 18(2):113-20 (2011)). Patients with recurrence after BCG therapy may present with urothelial carcinoma of the upper urinary tract or the prostatic urethra, which is not accessible to BCG. Also, patients with no measurable pre-existing T-cell immunity to BCG (due to previous BCG immunization or natural exposure to mycobacteria) have a lower recurrence-free survival rate (Biot, C., et al., *Sci Transl Med.*, June 6; 4(137):137ra72 (2012)). Patients with BCG-unresponsive non-muscle-invasive bladder cancer (NMIBC) have limited treatment options and the standard of care for these patients is radical cystectomy.

SUMMARY

Embodiments of the invention are directed to the treatment of bladder cancer utilizing, in particular aspects, antigen presenting cells, such as, for example, dendritic cells isolated from patients who have been administered an immunotherapeutic, such as *Bacillus* Calmette-Guerin (BCG). The antigen presenting cells are cultured ex vivo with an interleukin-15 (IL-15) based superagonist prior to administering to the subject. In certain embodiments, the dendritic cells are isolated from subjects who have not been treated with BCG.

In certain embodiments, a method for treating cancer comprises administering to the subject an effective dose of an immunotherapeutic agent; isolating an immune effector cell from the biological sample of the subject; culturing the immune effector cells with a composition comprising an IL-15:IL-15Rα fusion protein complex such as an IL-15N72D:IL-15RαSu/Fc complex, and reinfusing the cultured immune effector cells to the subject. In certain embodiments, the immunotherapeutic is BCG. In certain embodiments, the cultured immune effector cells are administered in combination with BCG and/or an IL-15 based superagonist and/or a chemotherapeutic agent.

In certain embodiments, a method for treating cancer comprises isolating an immune effector cell from a biological sample of the subject; culturing the immune effector cells with BCG and a composition comprising an IL-15:IL-15Rα fusion protein complex such as an IL-15N72D:IL-15RαSu/Fc complex, and reinfusing the cultured immune effector cells to the subject. In certain embodiments, the cultured immune effector cells are administered in combination with BCG and/or an IL-15 based superagonist and/or a chemotherapeutic agent.

In certain embodiments, a method of inducing an anti-bladder cancer immune response in a subject in need thereof, comprises administering to the subject an effective dose of *Bacillus* Calmette-Guerin (BCG); isolating dendritic cells from a urine sample of the subject; culturing the dendritic cells with a composition comprising an IL-15:IL-15Rα fusion protein complex such as an IL-15N72D:IL-15RαSu/Fc complex, reinfusing the dendritic cells to the subject, thereby inducing an anti-bladder cancer immune response.

In certain embodiments, a vaccine composition comprises *Bacillus* Calmette-Guerin (BCG) primed dendritic cells and an IL-15:IL-15Rα fusion protein complex such as an IL-15N72D:IL-15RαSu/Fc complex. In certain embodiments, the dendritic cells are isolated from a urine sample of a subject diagnosed with urothelial/bladder carcinoma. In certain embodiments, the vaccine composition comprises an adjuvant.

In certain embodiments, the IL-15 based superagonist comprises a dimeric IL-15RαSu/Fc and two IL-15N72D molecules. In certain aspects of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt), and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15RβγC receptors compared to the native IL-15 polypeptide. Alternatively, the IL-15 variant functions as an IL-15 antagonist as demonstrated by e.g., decreased binding activity for the IL-15RβγC receptors compared to the native IL-15 polypeptide.

In these and other embodiments, the immune effector cell comprises T cells, B cells, natural killer (NK) cells, natural killer T (NK-T) cells, dendritic cells, mast cells, myeloid-derived phagocytes or combinations thereof. In certain embodiments, the immune effector cell is a dendritic cell. In these and other embodiments, the immune effector cells comprising: autologous, allogeneic, haplotype matched, haplotype mismatched, haplo-identical, xenogeneic cells or combinations thereof.

In certain embodiments, the neoplastic disease or cancer comprises wherein the wherein cancer comprises bladder cancer, a glioblastoma, prostate cancer, hematological cancer, B-cell neoplasms, multiple myeloma, B-cell lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, colorectal cancer, ovarian cancer, non-small cell lung carcinoma, B cell non-Hodgkin lymphoma, and squamous cell head or neck carcinoma. In certain embodiments, the cancer is urothelial/bladder carcinoma.

In certain embodiments, the methods further comprise administering one or more chemotherapeutic agents.

In certain embodiments, a pharmaceutical composition comprises a therapeutically effective amount of an immunotherapeutic agent, and/or an IL-15N72D:IL-15RαSu/Fc complex (N-803). In certain embodiments the immunotherapeutic agent comprises *Bacillus* Calmette-Guerin (BCG) and the N-803 comprises a dimeric IL-15RαSu/Fc and two IL-15N72D molecules.

In certain embodiments, the treatment approaches of the invention could also be combined with any of the following therapies: radiation, chemotherapy, surgery, therapeutic antibodies, immunomodulatory agents, proteasome inhibitors, pan-DAC inhibitors, H-DAC inhibitors, checkpoint inhibitors, adoptive cell therapies include CAR T and NK cell therapy and vaccines.

Cell therapies of the invention comprise administration of an effective amount of immune effector cells. For example, an effective amount of dendritic cells is between $1\times10^4$ cells/kg and $1\times10^{10}$ cells/kg, e.g., $1\times10^3$, $1\times10^4$, $1\times10^5$, $1\times10^6$, $1\times10^7$, $1\times10^8$, $1\times10^9$, $1\times10^{10}$, $1\times10^{11}$, and $1\times10^{12}$ cells/kg, or such amounts that can be isolated by leukapheresis. Alternatively, expanded immune cells are administered as a fixed dose or based on body surface area (i.e., per $m^2$). Cells can be administered after ex vivo expansion or cryogenically preserved and administered after thawing (and washing as needed). The adoptively transferred immune effector cells or pharmaceutical compositions embodied herein, is administered at least one time per month, e.g., twice per month, once per week, twice per week, once per day, twice per day, every 8 hours, every 4 hours, every 2 hours, or every hour. Suitable modes of administration for the adoptively transferred immune cells include systemic administration, intravenous administration, or local administration. Suitable modes of administration for the pharmaceutical composition include systemic administration, intravenous administration, local administration, subcutaneous administration, intramuscular administration, intratumoral administration, inhalation, and intraperitoneal administration.

In certain embodiments, the dendritic cells are loaded with a tumor antigen, e.g. urothelial carcinoma antigens.

In some embodiments of the invention, the patient is pretreated or preconditioned to facilitate engraftment or survival of the adoptively transferred cells. Examples of preconditioning include treatment with cyclophosphamide and fludarabine. Additionally, the patient may be treated with agents that promote activation, survival or persistence of the adoptively transferred cells pre- and/or post-cell transfer.

Exemplary effective doses of the IL-15:IL-15Rα complex (N-803) include between 0.1 µg/kg and 100 mg/kg body weight, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, or 900 µg/kg body weight or 1, 2, 3, 4, 5, 6, 7, 8, 9, 10, 20, 30, 40, 50, 60, 70, 80, 90, or 100 mg/kg body weight.

In some cases, the N-803 and/or the BCG are administered daily, e.g., every 24 hours, or, continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

Exemplary effective daily doses of N-803 include between 0.1 µg/kg and 100 µg/kg body weight, e.g., 0.1, 0.3, 0.5, 1, 5, 10, 15, 20, 25, 30, 35, 40, 45, 50, 55, 60, 65, 70, 75, 80, 85, 90, 95, or 99 µg/kg body weight.

Alternatively, the N-803 is administered about once per week, e.g., about once every 7 days. Or, the N-803 is administered twice per week, three times per week, four times per week, five times per week, six times per week, or seven times per week. Exemplary effective weekly doses of N-803 include between 0.0001 mg/kg and 4 mg/kg body weight, e.g., 0.001, 0.003, 0.005, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, or 4 mg/kg body weight. For example, an effective weekly dose of N-803 is between 0.1 µg/kg body weight and 400 µg/kg body weight. Alternatively, N-803 is administered at a fixed dose or based on body surface area (i.e., per $m^2$).

In some cases, subjects receive two 6-week cycles consisting of 4 weekly N-803 intravenous doses followed by a 2-week rest period. Ultimately, the attending physician or veterinarian decides the appropriate amount and dosage regimen.

In certain embodiments, a kit for the treatment of bladder cancer comprises an effective amount of immune effector cells, an immunotherapeutic agent, and/or an IL-15N72D:IL-15RαSu/Fc complex (N-803), and directions for the treatment of bladder cancer. In certain embodiments the immunotherapeutic agent comprises *Bacillus* Calmette-Guerin (BCG) and the N-803 comprises a dimeric IL-15RαSu/Fc and two IL-15N72D molecules.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, small compound, nucleic acid based moiety, antibody, antibody-based molecule, protein, protein-based molecule and/or substance for use in the prevention, treatment, management and/or diagnosis of cancer.

By "N-803" is meant a complex comprising IL-15N72D noncovalently associated with a dimeric IL-15RαSu/Fc fusion protein and having immune stimulating activity. In one embodiment, the IL-15N72D and/or IL-15RαSu/Fc fusion protein comprises one, two, three, four or more amino acid variations relative to a reference sequence. An exemplary IL-15N72D amino acid sequence is provided below.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The invention includes antibodies or fragments of such antibodies, so long as they exhibit the desired biological activity. Also included in the invention are chimeric antibodies, such as humanized antibodies. Generally, a humanized antibody has one or more amino acid residues introduced into it from a source that is non-human. Humanization can be performed, for example, using methods described in the art, by substituting at least a portion of a rodent complementarity-determining region for the corresponding regions of a human antibody.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. F(ab')2, Fab', Fab, Fv) capable of binding the epitope, antigen or antigenic fragment of interest.

By "binding to" a molecule is meant having a physicochemical affinity for that molecule.

A "chemotherapeutic agent" is a chemical compound useful in the treatment of cancer. Examples of chemotherapeutic agents include Erlotinib (TARCEVA™, Genentech/OSI Pharm.), Bortezomib (VELCADE™, Millennium Pharm.), Fulvestrant (FASLODEX™, Astrazeneca), Sutent (SU11248, Pfizer), Letrozole (FEMARA™, Novartis), Imatinib mesylate (GLEEVEC™, Novartis), PTK787/ZK 222584 (Novartis), Oxaliplatin (Eloxatin™, Sanofi), 5-FU (5-fluorouracil), Leucovorin, Rapamycin (Sirolimus, RAPAMUNE™, Wyeth), Lapatinib (GSK572016, GlaxoSmithKline), Lonafarnib (SCH 66336), Sorafenib (BAY43-9006, Bayer Labs.), and Gefitinib (IRESSA™, Astrazeneca), AG1478, AG1571 (SU 5271; Sugen), alkylating agents such as Thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozcicsin, carzcicsin and bizcicsin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin omega 1 (*Angew Chem. Intl. Ed. Engl.* (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, strcptonigrin, strcptozocin, tubcrcidin, ubenimcx, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosinc; arabinoside ("Ara-C"); cyclophosphamide; thiotepa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX™ (tamoxifen)), raloxifene, droloxifene, 4-hydroxytamoxifen, trioxifene, keoxifene, LY117018, onapristone, and FARESTON™ (toremifene); (ii) aromatase inhibitors that inhibit the enzyme aromatase, which regulates estrogen production in the adrenal glands, such as, for example, 4(5)-imidazoles, aminoglutethimide, MEGASE™ (megestrol acetate), AROMASIN™ (exemestane), formestanie, fadrozole, RIVISOR™ (vorozole), FEMARA™ (letrozole), and ARIMIDEX™ (anastrozole); (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii) ribozymes such as a VEGF expression inhibitor (e.g., ANGIOZYME™ (ribozyme)) and a HER2 expression inhibitor; (ix) vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; (x) anti-angiogenic agents such as bevacizumab (AVASTIN™, Genentech); and (xi) pharmaceutically acceptable salts, acids or derivatives of any of the above.

"Detect" refers to identifying the presence, absence or amount of the analyte to be detected.

By "disease" is meant any condition or disorder that damages or interferes with the normal function of a cell, tissue, or organ. Examples of diseases include neoplasias.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

As used herein, the term "IL-15:IL-15Rα fusion protein complex" is a complex having IL-15 non-covalently or covalently bound to IL-15Rα. IL-15Rα can be either soluble or membrane bound. In some embodiments, IL-15Rα is the soluble domain of the native IL-15Rα polypeptide. The soluble IL-15Rα can be the IL-15Rα sushi domain or IL-15RαΔE3. In some cases, the soluble IL-15Rα is covalently linked to a biologically active polypeptide and/or to an IgG Fc domain. The IL-15 can be either IL-15 or IL-15 covalently linked to a second biologically active polypeptide. In some cases, IL-15 is covalently bound to the IL-15Rα domain via a linker. The IL-15 can also represent an IL-15 variant comprises one, two, three, four or more amino acid variations relative to a reference sequence. In one embodiment the IL-15 is IL-15N72D. In another embodiment, the IL-15:IL-15Rα fusion protein complex is N-803.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

The term "immune effector cell," as used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NK-T) cells, dendritic cells, mast cells, and myeloid-derived phagocytes. "Immune effector function or immune effector response," as that term is used herein, refers to function or response, e.g., of an immune effector cell, that enhances or promotes an immune attack of a target cell. For example, an immune effector function or response refers a property of a T or NK cell that promotes killing or the inhibition of growth or proliferation, of a target cell. In the case of a T cell, primary stimulation and co-stimulation are examples of immune effector function or response.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. An "isolated cell" e.g. a dendritic cell can be isolated from other cell populations, by for example, biomarkers. See, for example, Nair, S., Archer, G. E., & Tedder, T. F. (2012). Isolation and generation of human dendritic cells. *Current protocols in immunology*, Chapter 7, Unit 7.32. doi:10.1002/0471142735.im0732s99. Kits for isolating dendritic cells can be obtained from, STEMCELL Technologies Inc. Cambridge, Mass.

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to bladder cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, gastric and esophageal cancer, head and neck cancer, rectal cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In particular embodiments, the neoplasia is multiple myeloma, beta-cell lymphoma, urothelial/bladder carcinoma or melanoma.

As used herein, "obtaining" as in "obtaining an agent" includes synthesizing, purchasing, or otherwise acquiring the agent.

By "reduces" is meant a negative alteration of at least 5%, 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline. The subject is preferably a mammal in need of such treatment, e.g., a subject that has been diagnosed with B cell lymphoma or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

Treatment of patients with neoplasia may include any of the following: Adjuvant therapy (also called adjunct therapy or adjunctive therapy) to destroy residual tumor cells that may be present after the known tumor is removed by the initial therapy (e.g. surgery), thereby preventing possible cancer reoccurrence; neoadjuvant therapy given prior to the surgical procedure to shrink the cancer; induction therapy to cause a remission, typically for acute leukemia; consolidation therapy (also called intensification therapy) given once a remission is achieved to sustain the remission; maintenance therapy given in lower or less frequent doses to assist in prolonging a remission; first line therapy (also called standard therapy); second (or 3rd, 4th, etc.) line therapy (also called salvage therapy) is given if a disease has not responded or reoccurred after first line therapy; and palliative therapy (also called supportive therapy) to address symptom management without expecting to significantly reduce the cancer.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Certain methodologies of the instant invention include a step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a treatment and/or agent administration methodology, as described herein. For example, a transcription rate, mRNA level, translation rate, protein level, biological activity, cellular characteristic or property, genotype, phenotype, etc. can be determined prior to introducing a treatment and/or agent of the invention to a subject. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Genes: All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

Genbank and NCBI submissions indicated by accession number cited herein are incorporated herein by reference.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DETAILED DESCRIPTION

Embodiments of the invention are directed to inducing and/or enhancing an immune response to neoplastic diseases.

BCG therapy of bladder cancer results in extensive activation of the immune system. Within hours of BCG instillation, a marked increase in the number of leukocytes in the urine can be detected. These leukocytes consist mainly of granulocytes and, to a lesser degree, of macrophages and lymphocytes (De Boer, E. C. el al. Presence of activated lymphocytes in the urine of patients with superficial bladder cancer after intravesical immunotherapy with *Bacillus* Calmette-Guerin. *Cancer Immunol. Immunother.* 33, 411-416 (1991)). Similarly, an influx of immune cells can be found in the bladder wall after BCG therapy (Bohle A. et al., Effects of local *Bacillus* Calmette-Guerin therapy in patients with bladder carcinoma on immunocompetent cells of the bladder wall. *J. Urol.* 144, 53-58 (1990)). Additional evidence of immune activation is the release of a wide variety of cytokines and chemokines into the urine following BCG therapy (Redelman-Sidi G. et al, *Nat Rev Urol.* 2014 March; 11(3):153-62). Histopathologically, post-treatment bladder biopsies in patients treated with BCG reveal erosion of the superficial epithelium, and submucosal granulomatous inflammation, with oedema and non caseating granulomas surrounded by a lymphoplasmacytic and eosinophilic infiltrate (Lage, J. M. et al. Histological parameters and pitfalls in the interpretation of bladder biopsies in *Bacillus* Calmette-Guerin treatment of superficial bladder cancer. *J. Urol.* 135, 916-919 (1986)).

The majority of lymphocytes in the urine of patients treated with BCG are T cells, most of which are $CD4^+$ (De Boer, E. C. et al. Presence of activated lymphocytes in the urine of patients with superficial bladder cancer after intravesical immunotherapy with *Bacillus* Calmette-Guerin. *Cancer Immunol. Immunother.* 33, 411-416 (1991)). T cells, again mostly $CD4^+$, can also be found infiltrating the bladder mucosa for months after BCG therapy (Bohle, A. et al., *J. Urol.* 144, 53-58 (1990); Boccafoschi, C. et al. Immunophenotypic characterization of the bladder mucosa infiltrating lymphocytes after intravesical BCG treatment for superficial bladder carcinoma. *Eur. Urol.* 21, 304-308 (1992)). Although $CD4^+$ lymphocytes predominate, both $CD4^+$ and $CD8^+$ lymphocytes seem to be required for effective BCG therapy.

The cytotoxicity of BCG-specific NK cells, which have also been termed BCG-activated killer (BAK) cells (Brandau, S. & Bohle, A. Activation of natural killer cells by *Bacillus* Calmette-Guerin. *Eur. Urol.* 39, 518-524 (2001)), can be enhanced by IL-12 and interferon (IFN)-γ, and is inhibited by IL-1 (Suttmann, H. et al. Mechanisms of *Bacillus* Calmette-Guerin mediated natural killer cell activation. *J. Urol.* 172, 1490-1495 (2004)). Killing of bladder cancer cells by BAK cells seems to involve perforin, which is a cytolytic protein that is released from granules and forms a pore in the plasma membrane of the target cell (Brandau, S. et al. Perforin-mediated lysis of tumor cells by *Mycobacterium bovis Bacillus* Calmette-Guerin-activated killer cells. *Clin. Cancer Res.* 6, 3729-3738 (2000)).

Dendritic cells have been postulated to initiate activation of T cells after BCG administration. Although some evidence from in vitro studies supports this hypothesis, a role for dendritic cells in response to BCG has not been clearly defined. Immature dendritic cells have been identified in the urine of patients with bladder cancer who were treated with BCG (Beatty, J. D. et al. Urine dendritic cells: a noninvasive probe for immune activity in bladder cancer? *BJU Int.* 94, 1377-1383 (2004)), and in vitro, dendritic cells that were exposed to BCG can activate NK cells and γδ T cells, and induce their cytotoxicity against BCG-infected bladder cancer cells (Naoe, M. et al. *Bacillus* Calmette-Guerin-pulsed dendritic cells stimulate natural killer T cells and gamma delta T cells. *Int. J Urol.* 14, 532-538 (2007); Higuchi, T. et al. A possible mechanism of intravesical BCG therapy for human bladder carcinoma: involvement of innate effector cells for the inhibition of tumor growth. *Cancer Immunol. Immunother.* 58, 1245-1255 (2009)). Similar to the finding for tumor-associated macrophages, patients with high levels of tumor-associated dendritic cells prior to BCG treatment were more likely to experience cancer recurrence after BCG therapy (Ayari, C. et al. Bladder tumor infiltrating mature dendritic cells and macrophages as predictors of response to *Bacillus* Calmette-Guerin immunotherapy. *Eur. Urol.* 55, 1386-1395 (2009)). As is the case with tumor-associated macrophages, this finding might be explained by immunosuppression induced by specific subsets of tumor-associated dendritic cells (Hurwitz, A. A. & Watkins, S. K. Immune suppression in the tumor microenvironment: a role for dendritic cell-mediated tolerization of T cells. *Cancer Immunol. Immunother.* 61, 289-293 (2012)).

BCG therapy is followed by a massive release of cytokines into the urine of treated patients. These cytokines include IL-1, IL-2, IL-5, IL-6, IL-8, IL-10, IL-12, IL-18, TNF, IFN-γ, and granulocyte-macrophage colony-stimulating factor (GM-CSF) (De Boer, E. C. et al. *Cancer Immunol. Immunother.* 34, 306-312 (1992); Eto, M. et al. Importance of urinary interleukin-18 in intravesical immunotherapy with *Bacillus* Calmette-Guerin for superficial bladder tumors. *Urol. Int.* 75, 114-118 (2005)), as well as the chemokines macrophage-derived chemokine (MDC), monocyte chemoattractant protein (MCP)-1, MIP-1α, and interferon-inducible protein (IP)-10 (Luo, Y., et al. *Mycobacterium bovis Bacillus* Calmette-Guerin (BCG) induces human CC- and CXC-chemokines in vitro and in vivo. *Clin. Exp. Immunol.* 147, 370-378 (2007)). Although the array of cytokines found in the urine of patients treated with BCG cannot be strictly categorized as corresponding to a $T_H1$ or $T_H2$ response, the presence of IL-2, IL-12, and IFN-γ, and the absence of IL-4, are more consistent with a $T_H1$-like response. Another cytokine that has been evaluated in response to BCG is TRAIL, a member of the TNF family that is expressed by various immune cells, including cytotoxic lymphocytes, NK cells, and neutrophils.

In addition to the local inflammatory response in the bladder wall, BCG therapy induces a systemic immune response. More than 40% of patients receiving intra-vesical BCG instillation experience conversion of a previously negative tuberculin skin test (Kelley, D. R. et al. Prognostic value of purified protein derivative skin test and granuloma formation in patients treated with intravesical *Bacillus* Calmette-Guerin. *J. Urol.* 135, 268-271 (1986)). Furthermore, patients treated with BCG have increased serum levels of IL-2 and IFN-γ, and peripheral blood mononuclear cells in patients who have received repeated instillations of BCG exhibit increased killing activity against an NK-cell resistant cancer cell line, compared with before BCG treatment (Taniguchi, K. et al. Systemic immune response after intravesical instillation of *Bacillus* Calmette-Guerin (BCG) for superficial bladder cancer. *Clin. Exp. Immunol.* 115, 131-135 (1999)).

The immune response to BCG is preceded by an interaction between BCG and urothelial cells, which is essential to achieving antitumor activity. The initial step is attachment of BCG to urothelial cells. This step is facilitated by fibronectin, a glycoprotein that is part of the extracellular matrix and that can also be found in urine in a soluble form. BCG attaches to fibronectin through its fibronectin attachment protein (FAP) (Zhao, W. et al. Role of a *Bacillus* Calmette-Guerin fibronectin attachment protein in BCG-induced antitumor activity. *Int. J. Cancer* 86, 83-88 (2000)). In turn, fibronectin is thought to attach to urothelial cells through integrin α5β1 (Coplen, D. E., et al. Characterization of fibronectin attachment by a human transitional cell carcinoma line, T24. *J. Urol.* 145, 1312-1315 (1991)). In vitro, BCG attachment and internalization is enhanced by addition of exogenous fibronectin and inhibited by antibodies against fibronectin or integrins α5 or β1 (Kuroda, K., et al. Characterization of the internalization of *Bacillus* Calmette-Guerin by human bladder tumor cells. *J. Clin. Invest.* 91, 69-76 (1993)).

Bladder cancer cells can directly secrete immune-activating effectors following internalization of BCG. The main cytokine studied in this context has been IL-6, which is released from bladder cancer cells exposed to BCG.

Dendritic Cells

Dendritic Cells (DC) are the most powerful antigen presenting cells of the immune system, capable of stimulating naïve and memory CD8$^+$ T-cells as well as B-cells and CD4$^+$ helper T-cells. In the immature state DC are present in blood and tissues, processing foreign antigens for presentation to the immune system. The uptake of presentable antigen stimulates maturation of DC and promotes DC migration to lymph nodes, where these cells can directly interact with immune effector cells. Mature DC are capable of stimulating T helper type-1 immune responses and antigen specific CD8$^+$ cytotoxic T-lymphocytes (CTL), but within the tumor microenvironment DC promote tumor tolerance, facilitating T helper type-2 responses. Therefore DC can exert both strong positive and negative influences on the acquisition of tumor specific cellular immune responses.

DC vaccines have generally consisted of autologous monocytes that are matured in vitro and pulsed with antigen before injection. Each step of DC vaccine production, DC generation, antigen loading, in vitro maturation, and inoculation with or without adjuvant is an opportunity to enhance efficacy. DC vaccine research has therefore focused on expanding the available sources of DC and improving DC immunogenicity, optimizing the source and presentation of antigen, developing new immune adjuvants, and investigation of concomitant immunomodulation or chemotherapy. (Kalijn F. Bol et al. "Dendritic Cell-Based Immunotherapy: State of the Art and Beyond." *Clinical Cancer Research*, 2016; 22:1897-1906; Elster, Jennifer D et al. "Dendritic cell vaccines: A review of recent developments and their potential pediatric application." Human Vaccines & Immunotherapeutics vol. 12, 9 ( ): 2232-9. doi:10.1080/21645515.2016.1179844).

Interleukin-15

IL-15 is a pleiotropic cytokine that plays various roles in the innate and adaptive immune systems, including the development, activation, homing and survival of immune effector cells, especially NK, NK-T and CD8$^+$ T cells (Cooper, M. A., et al., *Blood*, 2001. 97(10): p. 3146-51). IL-15, a member of the common gamma chain (γc) cytokine family, binds to a receptor complex that consists of IL-15Rα, IL-2Rβ and the γc chain (Grabstein, K. H., et al., *Science*, 1994. 264(5161): p. 965-8; Giri, J. G., et al., *Embo J*, 1995. 14(15): p. 3654-63). Furthermore, IL-15 functions as a key regulator of development, homeostasis and activity of NK cells (Prlic, M., et al., *J Exp Med*, 2003. 197(8): p. 967-76; Carson, W. E., et al., *J Clin Invest*, 1997. 99(5): p. 937-43). IL-15 administration to normal mice or overexpression of IL-15 in the transgenic mouse model increases the number and percentage of NK cells in the spleen (Evans, R., et al., *Cell Immunol*, 1997. 179(1): p. 66-73; Marks-Konczalik, J., et al., *Proc Natl Acad Sci USA*, 2000. 97(21): p. 11445-50), the proliferation and survival of NK cells, as well as their cytolytic activity and cytokine secretion. IL-15 administration could also increase the NK cell number and function in recipients of stem cell transplantation (Katsanis, E., et al., *Transplantation*, 1996. 62(6): p. 872-5; Judge, A. D., et al., *J Exp Med*, 2002. 196(7): p. 935-46; Alpdogan, O., et al., *Blood*, 2005. 105(2): p. 865-73; Sauter, C. T., et al., *Bone Marrow Transplantation*, 2013. 48(9): p. 1237-42).

The primary limitations in clinical development of recombinant human IL-15 (rhIL-15) are low production yields in standard mammalian cell expression systems and a short serum half-life (Ward, A., et al., *Protein Expr Purif*, 2009. 68(1): p. 42-8; Bessard, A., et al., *Mol Cancer Ther*, 2009. 8(9): p. 2736-45). The formation of the IL-15:IL-15Rα complex, with both proteins co-expressed in the same cell can stimulate immune effector cells bearing the IL-2βγc receptor through a trans-presentation mechanism. In addition, when IL-15 is bound to IL-15Rα, it increased the affinity of the IL-15 to IL-2Rβ approximately 150-fold, when compared with free IL-15 (Ring, A. M., et al., *Nat Immunol*, 2012. 13(12): p. 1187-95). A superagonist mutant of IL-15 (IL-15N72D), which has increased IL-2Rβ binding ability (4-5 fold higher than native IL-15) has been identified for therapeutic usages (Zhu, X., et al., Novel human interleukin-15 agonists. *J Immunol*, 2009. 183(6): p. 3598-607). The strong interaction of IL-15N72D and soluble IL-15Rα was exploited to create an IL-15 superagonist complex with IL-15N72D bound to IL-15RαSu/Fc. The soluble fusion protein, IL-15RαSu/Fc, was created by linking the human IL-15RαSu domain with human IgG1 containing the Fc domain. Studies on IL-15:IL-15Rα complexes show an advantage of increased intracellular stability of IL-15 (Bergamaschi, C., et al., *J Biol Chem*, 2008. 283(7): p. 4189-99; Duitman, E. H., et al., *Mol Cell Biol*, 2008. 28(15): p. 4851-61). Co-expression of both the IL-15N72D and IL-15RαSu/Fc proteins resulted in a soluble and stable complex with significantly longer serum half-life and increased biological activity, compared to native IL-15 (Han, K. P., et al., *Cytokine*, 2011. 56(3): p. 804-10). As indicated above, this IL-15N72D:IL-15RαSu/Fc complex (N-803) was >10-fold more active than free IL-15 in promoting in vitro proliferation of IL-15-dependent cells (Zhu, X., et al., Novel human interleukin-15 agonists. *J Immunol*, 2009. 183(6): p. 3598-607). N-803 has potent anti-tumor activity in syngeneic murine models of multiple myeloma (Xu, W., et al., *Cancer Res*, 2013. 73(10): p. 3075-86).

IL-15:IL-15Rα Complex

As defined above, an IL-15:IL-15Rα fusion protein complex can refer to a complex having IL-15 non-covalently bound to the soluble IL-15Rα domain of the native IL-15Rα. In some cases, the soluble IL-15Ra is covalently linked to a biologically active polypeptide and/or to an IgG Fc domain. The IL-15 can be either IL-15 or IL-15 covalently linked to a second biologically active polypeptide. The crystal structure of the IL-15:IL-15Rα complex is shown in Chirifu et al., 2007 *Nat Immunol* 8, 1001-1007, incorporated herein by reference.

In certain embodiments, the IL-15Rα comprises IL-15RαSushi (IL-15RαSu). In other embodiments, the IL-15 is a variant IL-15 (e.g., IL-15N72D).

In certain embodiments of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt) and variants thereof are referred to using the native amino acid, its position in the mature sequence and the variant amino acid. For example, huIL15N72D refers to human IL-15 comprising a substitution of N to D at position 72. In certain embodiments, the IL-15 variant functions as an IL-15 agonist as demonstrated, e.g., by increased binding activity for the IL-15RβγC receptors compared to the native IL-15 polypeptide. In certain embodiments, the IL-15 variant functions as an IL-15 antagonist as demonstrated by e.g., decreased binding activity for the IL-15RβγC receptors compared to the native IL-15 polypeptide. In certain embodiments, the IL-15 variant has increased binding affinity or a decreased binding activity for the IL-15RβγC receptors compared to the native IL-15 polypeptide. In certain embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution or deletion in the domain of IL-15 that interacts with IL-15Rβ and/or IL-15RγC. In certain embodiments, the amino acid change is one or more amino acid substitutions or deletions at position 8, 61, 65, 72, 92, 101, 108, or 111 of the mature human IL-15 sequence. For example, the amino acid change is the substitution of D to N or A at position 8, D to A at position 61, N to A at position 65, N to R at position 72 or Q to A at position 108 of the mature human IL-15 sequence, or any combination of these substitutions. In certain embodiments, the amino acid change is the substitution of N to D at position 72 of the mature human IL-15 sequence.

N-803

N-803 comprises an IL-15 mutant with increased ability to bind IL-2Rβγ and enhanced biological activity (U.S. Pat. No. 8,507,222, incorporated herein by reference). This super-agonist mutant of IL-15 was described in a publication (*J. Immunol* 2009 183:3598) and a patent has been issued by the U.S. Patent & Trademark Office on the super agonist and several patents applications are pending (e.g., U.S. Ser. Nos. 12/151,980 and 13/238,925). This IL-15 super-agonist in combination with a soluble IL-15α receptor fusion protein (IL-15RαSu/Fc) results in a protein complex with highly potent IL-15 activity in vitro and in vivo (Han et al., 2011, *Cytokine,* 56: 804-810; Xu, et al., 2013 *Cancer Res.* 73:3075-86, Wong, et al., 2013, *OncoImmunology* 2:e26442). This IL-15 super agonist complex (IL-15N72D:IL-15RαSu/Fc) is referred to as N-803. Pharmacokinetic analysis indicated that the complex has a half-life of 25 hours following i.v. administration in mice. N-803 exhibits impressive anti-tumor activity against aggressive solid and hematological tumor models in immunocompetent mice. It can be administered as a monotherapy using a twice weekly or weekly i.v. dose regimen or as combinatorial therapy with an antibody. The N-803 anti-tumor response is also durable. Tumor-bearing mice that were cured after N-803 treatment were also highly resistant to re-challenge with the same tumor cells indicating that N-803 induces effective immunological memory responses against the re-introduced tumor cells.

Fc Domain

N-803 comprises an IL-15N72D:IL-15RαSu/Fc fusion complex. Fusion proteins that combine the Fc regions of IgG with the domains of another protein, such as various cytokines and soluble receptors have been reported (see, for example, Capon et al., *Nature,* 337:525-531, 1989; Chamow et al., *Trends Biotechnol.,* 14:52-60, 1996; U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_{H1}$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15RαSu covalently linked to the Fc portion of the human heavy chain IgG protein have been made (e.g., N-803).

The term "Fc" refers to a non-antigen-binding fragment of an antibody. Such an "Fc" can be in monomeric or multimeric form. The original immunoglobulin source of the native Fc is preferably of human origin and may be any of the immunoglobulins, although IgG 1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10: 4071-9). The term "native Fc" as used herein is generic to the monomeric, dimeric, and multimeric forms. Fc domains containing binding sites for Protein A, Protein G, various Fc receptors and complement proteins.

In some embodiments, the term "Fc variant" refers to a molecule or sequence that is modified from a native Fc, but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) antibody-dependent cell-mediated cytotoxicity (ADCC), or (8) antibody dependent cellular phagocytosis (ADCP). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Linkers

In some cases, the fusion protein complexes of the invention also include a flexible linker sequence interposed between the IL-15 or IL-15Rα domains. The linker sequence should allow effective positioning of the polypeptide with respect to the IL-15 or IL-15Rα domains to allow functional activity of both domains.

In certain cases, the soluble fusion protein complex has a linker wherein the first polypeptide is covalently linked to IL-15 (or functional fragment thereof) by a polypeptide linker sequence. In other aspects, the soluble fusion protein complex as described herein has a linker wherein the second polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. For example, the IL-15 or IL-15Rα domains are effectively positioned to allow interactions with immune cells to initiate or inhibit an immune reaction, or to inhibit or stimulate cell development.

The fusion protein complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. For example, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generate a single-chain molecule with the desired functional activity.

Preferably, the linker sequence comprises from about 7 to 20 amino acids, more preferably from about 10 to 20 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine and serine, to provide for flexibility. Preferably, about 80 or 90 percent or greater of the linker sequence comprises glycine, alanine or serine residues, particularly glycine and serine residues.

Different linker sequences could be used including any of a number of flexible linker designs that have been used successfully to join antibody variable regions together (see, Whitlow, M. et al., (1991) Methods: A Companion to Methods in Enzymology, 2:97-105).

Fusions Protein Complexes

The invention provides N-803, which is a protein complex between IL-15N72D and IL-15RαSu/Fc. An exemplary IL-15N72D nucleic acid sequence is provided below (with leader peptide) (SEQ ID NO: 1):

(Leader peptide)
atggagacagacacactcctgttatgggtactgctgctctgggttccagg ttccaccggt- (IL-15N72D)
aactgggtgaatgtaataagtgatttgaaaaaaattgaagatcttattca atctatgcatattgatgctactttatatacggaaagtgatgttcacccca gttgcaaagtaacagcaatgaagtgtgtttctcttggagttacaagttatt tcacttgagtccggagatgcaagtattcatgatacagtagaaaatctgat catcctagcaaacgacagtttgtcttctaatgggaatgtaacagaatctg gatgcaaagaatgtgaggaactggaggaaaaaaatattaaagaattttg cagagttttgtacatattgtccaaatgttcatcaacacttct (Stop codon)
taa An exemplary IL-15N72D amino acid sequence is provided below (with leader peptide) (SEQ ID NO: 2):

(Leader peptide)
METDTLLLWVLLLWVPGSTG- (IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

In some cases, the leader peptide is cleaved from the mature IL-15N72D polypeptide (SEQ ID NO: 3):

(IL-15N72D)
NWVNVISDLKKIEDLIQSMHIDATLYTESDVHPSCKVTAMKCFLLELQVI

SLESGDASIHDTVENLIILANDSLSSNGNVTESGCKECEELEEKNIKEFL

QSFVHIVQMFINTS

An exemplary IL-15RαSu/Fc nucleic acid sequence (with leader peptide) is provided below (SEQ ID NO: 4):

(Leader peptide)
atggacagacttacttcttcattcctgctcctgattgtccctgcgtacgt cttgtcc- (IL-15RαSu)
atcacgtgccctcccccatgtccgtggaacacgcagacatctgggtcaa gagctacagcttgtactccagggagcggtacatttgtaactctggtttca agcgtaaagccggcacgtccagcctgacggagtgcgtgttgaacaaggcc acgaatgtcgcccactggacaaccccagtctcaaatgtattaga- (IgG1 CH2-CH3 (Fc domain))
gagcccaaatcttgtgacaaaactcacacatgcccaccgtgcccagcacc tgaactcctggggggaccgtcagtcttcctcttccccccaaaacccaagg acaccctcatgatctcccggacccctgaggtcacatgcgtggtggtggac gtgagccacgaagaccctgaggtcaagttcaactggtacgtggacggcgt ggaggtgcataatgccaagacaaagccgcgggaggagcagtacaacagca cgtaccgtgtggtcagcgtcctcaccgtcctgcaccaggactggctgaat ggcaaggagtacaagtgcaaggtctccaacaaagccctcccagcccccat cgagaaaaccatctccaaagccaaagggcagccccgagaaccacaggtgt acaccctgcccccatcccgggatgagctgaccaagaaccaggtcagcctg acctgcctggtcaaaggcttctatcccagcgacatcgccgtggagtggga gagcaatgggcagccggagaacaactacaagaccacgcctcccgtgctgg

```
                          -continued
actccgacggctccttcttcctctacagcaagctcaccgtggacaagagc aggtggcagcagggaacgtcttctcatgctccgtgatgcatgaggctct gcacaaccactacacgcagaagagcctctccctgtctccgggtaaa- (Stop codon)
taa
```

An exemplary IL-15RαSu/Fc amino acid sequence (with leader peptide) is provided below (SEQ ID NO: 5):

```
(Leader peptide)
MDRLTSSFLLLIVPAYVLS- (IL-15RαSu)
ITCPPPMSVEHADIWVKSYSLYSRERYICNSGFKRKAGTSSLTECVLNKA

TNVAHWTTPSLKCIR- (IgG1 CH2-CH3 (Fc domain))
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

In some cases, the mature IL-15RαSu/Fc protein lacks the leader sequence (SEQ ID NO: 6):

```
(IL-15RαSu)
ITCPPPMSVEHADIWVKSYSLYSRERYICNSGFKRKAGTSSLTECVLNKA

TNVAHWTTPSLKCIR- (IgG1 CH2-CH3 (Fc domain))
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

*Bacillus* Calmette-Guerin (BCG)

*Bacillus* Calmette-Guérin (BCG), a live attenuated strain of *Mycobacterium bovis*, is currently the only agent approved by the US Food and Drug Administration for primary therapy of carcinoma in situ (CIS) of the bladder. The original *Bacillus* Calmette-Guérin (BCG) strain was developed at the Pasteur Institute from an attenuated strain of *Mycobacterium bovis*. Two BCG products are commercially available in the United States. The Tice strain, which is a substrain of the original Pasteur product, is manufactured by Organon Pharmaceuticals. The TheraCys strain is made by Aventis/Pasteur. BCG supplanted cystectomy as the treatment of choice for CIS in the mid-1980s. BCG therapy also reduces the risk of recurrence, and ongoing maintenance therapy with BCG reduces the risk of progression in patients with high-grade non-muscle invasive bladder cancer.

Bladder cancer is the only cancer in which BCG is commonly used. For BCG to be effective, all the following criteria should be met: The patient is immunocompetent, the tumor burden is small; BCG makes direct contact with the tumor, the dose is adequate to incite a reaction.

BCG viability is an important consideration for the vaccine to be effective. This viability is measured in colony-forming units (CFUs). A vaccine that contains no or very few live organisms would be clinically ineffective. One dose, either an ampule or vial, may vary in weight from one product to another, but the CFU should be similar. Tice BCG has $1-8 \times 10^{-8}$ CFUs. TheraCys has $10.5 +/- 8.7 \times 10^{-8}$ CFUs.

Typically, BCG is administered in either an induction (once weekly for 6 weeks) or maintenance (once weekly for 3 weeks) course. Another 6-week course may be administered if a repeat cystoscopy (see image above) reveals tumor persistence or recurrence. Induction therapy combined with maintenance therapy every 3-6 months for 1-3 years may provide more lasting results. Periodic bladder biopsies are usually necessary to assess response. Accordingly, the administration of BCG and/or N-803 can be determined based on the progress of the patient. The guidelines from the American Urological Association (AUA) and the Society of Urologic Oncology (SUO) (Chang S S, et al. Diagnosis and Treatment of Non-Muscle Invasive Bladder Cancer: AUA/SUO Guideline. *J Urol.* 2016 October 196 (4):1021-9) provide further guidance on the administration of BCG.

Formulation of Pharmaceutical Compositions

The administration of compositions embodied herein, such as, immune effector cells, e.g. dendritic cells, BCG-primed dendritic cells, BCG-primed dendritic cells cultured with N-803, or immunotherapeutic agents e.g. N-803 and/or BCG for the treatment of a neoplasia may be by any suitable means that results in a concentration of the therapeutic that, combined with other components, is effective in ameliorating, reducing, or stabilizing a neoplasia, e.g. bladder cancer. The N-803 and BCG may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, intravesicularly or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice or nonhuman primates, as a skilled artisan recognizes it is routine in the art to modify the dosage for humans compared to animal models. In certain embodiments it is envisioned that the dosage may vary from between about 0.1 µg compound/kg body weight to about 5000 µg compound/kg body weight; or from about 1 µg/kg body weight to about 4000 µg/kg body weight or from about 10 µg/kg body weight to about 3000 µg/kg body weight. In other embodiments this dose may be about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 µg/kg body weight. In other embodiments, it is envisaged that doses may be in the range of about 0.5 µg compound/kg body weight to about 20 µg compound/kg body weight. In other embodiments the doses may be about 0.5, 1, 3, 6, 10, or 20 mg/kg body weight. Of course, this dosage amount may be adjusted upward or downward, as is routinely done in such treatment protocols, depending on the results of the initial clinical trials and the needs of a particular patient.

In particular embodiments, N-803 are formulated in an excipient suitable for parenteral or intravesical administration. In particular embodiments, N-803 is administered at 0.5 µg/kg-about 15 µg/kg (e.g., 0.5, 1, 3, 5, 10, or 15 µg/kg).

For the treatment of bladder cancer, N-803 is administered by instillation into the bladder. Methods of instillation are known. See, for example, Lawrencia, et al., *Gene Ther* 8, 760-8 (2001); Nogawa, et al., *J Clin Invest* 115, 978-85 (2005); Ng, et al., *Methods Enzymol* 391, 304-13 2005; Tyagi, et al., *J Urol* 171, 483-9 (2004); Trevisani, et al., *J Pharmacol Exp Ther* 309, 1167-73 (2004); Trevisani, et al., *Nat Neurosci* 5, 546-51 (2002)). In certain embodiments, it is envisioned that the N-803 dosage for instillation may vary from between about 5 and 1000 µg/dose. In other embodiments the intravesical doses may be about 25, 50, 100, 200, or 400 µg/dose. In other embodiments, N-803 is administered by instillation into the bladder in combination with standard therapies, including mitomycin C or BCG.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical compositions embodied herein, such as, immune effector cells, e.g. dendritic cells, BCG-primed dendritic cells, BCG-primed dendritic cells cultured with N-803, or immunotherapeutic agents e.g. N-803 and/or BCG may be administered parenterally by injection, infusion or implantation (subcutaneous, intravenous, intramuscular, intravesicularly, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions embodied herein, such as, immune effector cells, e.g. dendritic cells, BCG-primed dendritic cells, BCG-primed dendritic cells cultured with N-803, or immunotherapeutic agents e.g. N-803 and/or BCG for intravesical or parenteral use may be provided in unit dosage forms (e.g., in single-dose ampoules, syringes or bags), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions comprising N-803 and/or BCG may be in a form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The present invention provides methods of treating neoplastic and/or disorders or symptoms thereof which comprise administering a therapeutically effective amount of a pharmaceutical composition comprising a composition embodied herein, such as, immune effector cells, e.g. dendritic cells, BCG-primed dendritic cells, BCG-primed dendritic cells cultured with N-803, or immunotherapeutic agents e.g. N-803 and/or BCG herein to a subject (e.g., a mammal such as a human). Thus, one embodiment is a method of treating a subject suffering from or susceptible to a neoplastic or disorder or symptom thereof. The method includes the step of administering to the mammal a therapeutic amount of an amount of a composition embodied herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). N-803 may be used in the treatment of any other disorders in which an increase in an immune response is desired.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

The compositions embodied herein, such as, immune effector cells, e.g. dendritic cells, BCG-primed dendritic cells, BCG-primed dendritic cells cultured with N-803, or immunotherapeutic agents e.g. N-803 and/or BCG, can be administered in combination with an anti-neoplasia such as a chemotherapeutic agent, e.g. mitomycin C, an antibody, e.g., a tumor-specific antibody or an immune-checkpoint inhibitor. The compositions may be administered simultaneously or sequentially. In some embodiments, the chemotherapeutic treatment is an established therapy for the disease indication and addition of, for example, dendritic cells isolated from a subject, the treatment improves the therapeutic benefit to the patients. Such improvement could be measured as increased responses on a per patient basis or increased responses in the patient population. Combination therapy could also provide improved responses at lower or less frequent doses of chemotherapeutic agent resulting in a better tolerated treatment regimen.

If desired, the immune effector cells, e.g. dendritic cells obtained from subjects having been administered BCG and cultured with N-803, are administered in combination with any conventional therapy, including but not limited to, surgery, radiation therapy, chemotherapy, protein-based therapy or biological therapy. Chemotherapeutic drugs include alkylating agents (e.g., platinum-based drugs, tetrazines, aziridines, nitrosoureas, nitrogen mustards), anti-metabolites (e.g., anti-folates, fluoropyrimidines, deoxynucleoside analogues, thiopurines), anti-microtubule agents (e.g., Vinca alkaloids, taxanes), topoisomerase inhibitors (e.g., topoisomerase I and II inhibitors), cytotoxic antibiotics (e.g., anthracyclines) and immunomodulatory drugs (e.g., thalidomide and analogs).

Anti-Cancer Therapeutic Agents

The methods of the invention may include administration of second therapeutic agent or treatment with a second therapy (e.g., a therapeutic agent or therapy that is standard in the art). Exemplary therapeutic agents include chemotherapeutic agents. A "chemotherapeutic agent" is a chemical compound useful in the treatment of cancer. Examples of chemotherapeutic agents include mitomycin C, Erlotinib (TARCEVA™, Genentech/OSI Pharm.), Bortezomib (VELCADE™, Millennium Pharm.), Fulvestrant (FASLODEX™, Astrazeneca), Sutent (SU11248, Pfizer), Letrozole (FEMARA™, Novartis), Imatinib mesylate (GLEEVEC™, Novartis), PTK787/ZK 222584 (Novartis), Oxaliplatin (Eloxatin™, Sanofi), 5-FU (5-fluorouracil), Leucovorin, Rapamycin (Sirolimus, RAPAMUNE™, Wyeth), Lapatinib (GSK572016, GlaxoSmithKline), Lonafarnib (SCH 66336), Sorafenib (BAY43-9006, Bayer Labs.), and Gefitinib (IRESSA™, Astrazeneca), AG1478, AG1571 (SU 5271; Sugen), alkylating agents such as Thiotepa and CYTOXAN™ cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozcicsin, carzcicsin and bizcicsin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin omega 1 (*Angew Chem. Intl. Ed. Engl.* (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX™ (tamoxifen)), raloxifene, droloxifene, 4-hydroxytamoxifen, trioxifene, keoxifene, LY117018, onapristone, and FARESTON™ (toremifene); (ii) aromatase inhibitors that inhibit the enzyme aromatase, which regulates estrogen production in the adrenal glands, such as, for example, 4(5)-imidazoles, aminoglutethimide, MEGASE™ (megestrol acetate), AROMASIN™ (exemestane), formestanie, fadrozole, RIVISOR™ (vorozole), FEMARA™ (letrozole), and ARIMIDEX™ (anastrozole); (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii) ribozymes such as a VEGF expression inhibitor (e.g., ANGIOZYME™ (ribozyme)) and a HER2 expression inhibitor; (ix) vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; (x) anti-angiogenic agents such as bevacizumab (AVASTIN™, Genentech); and (xi) pharmaceutically acceptable salts, acids or derivatives of any of the above.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A vaccine composition comprising 1) *Bacillus* Calmette-Guerin (BCG) primed dendritic cells, wherein the dendritic cells are isolated from a biological sample of an intravesical BCG-treated subject and 2) an IL-15:IL-15Rα fusion protein complex, wherein the dendritic cells are exposed ex-vivo to the IL-15:IL-15Rα fusion protein complex.

2. The vaccine composition of claim 1 wherein the IL-15:IL-15Rα complex comprises an IL-15N72D:IL-15RαSu/Fc complex.

3. The vaccine composition of claim 2, wherein the IL-15N72D:IL-15RαSu/Fc complex comprises a dimeric IL-15RαSu/Fc and two IL-15N72D molecules.

4. The vaccine composition of claim 1, wherein the dendritic cells are isolated from a subject diagnosed with urothelial/bladder carcinoma.

5. The vaccine composition of claim 1, further comprising an adjuvant.

6. The vaccine composition of claim 1, wherein the composition further comprises urothelial/bladder carcinoma antigens.

7. The vaccine composition of claim 2, wherein the IL-15N72D:IL-15RαSu/Fc complex is N-803.

8. The vaccine composition of claim 1, wherein the vaccine is formulated in an administration mode selected from the group consisting of systemic, intravenous, local, subcutaneous, intramuscular, inhalation and intraperitoneal.

9. The vaccine composition of claim 1, wherein the dendritic cells are isolated from a urine sample of the subject.

\* \* \* \* \*

SEQUENCE LISTING

```
<160> NUMBER OF SEQ ID NOS: 6

<210> SEQ ID NO 1
<211> LENGTH: 405
<212> TYPE: DNA
<213> ORGANISM: Artificial Sequence
<220> FEATURE:
<223> OTHER INFORMATION: Synthetic polynucleotide

<400> SEQUENCE: 1
atggagacag acacactcct gttatgggta ctgctgctct gggttccagg ttccaccggt      60
aactgggtga atgtaataag tgatttgaaa aaaattgaag atcttattca atctatgcat     120
attgatgcta ctttatatac ggaaagtgat gttcacccca gttgcaaagt aacagcaatg     180
aagtgctttc tcttggagtt acaagttatt tcacttgagt ccgagatgc aagtattcat      240 gatacagtag aaaatctgat catcctagca aacgacagtt tgtcttctaa tgggaatgta     300
acagaatctg gatgcaaaga atgtgaggaa ctggaggaaa aaaatattaa agaattttg      360 cagagttttg tacatattgt ccaaatgttc atcaacactt cttaa                     405

<210> SEQ ID NO 2
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 2

Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
            20                  25                  30

Glu Asp Leu Ile Gln Ser Met His Ile Asp Ala Thr Leu Tyr Thr Glu
        35                  40                  45

Ser Asp Val His Pro Ser Cys Lys Val Thr Ala Met Lys Cys Phe Leu
```

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asp Ser Leu Ser Ser
                85                  90                  95

Asn Gly Asn Val Thr Glu Ser Gly Cys Lys Glu Cys Glu Glu Leu Glu
            100                 105                 110

Glu Lys Asn Ile Lys Glu Phe Leu Gln Ser Phe Val His Ile Val Gln
        115                 120                 125

Met Phe Ile Asn Thr Ser
    130

<210> SEQ ID NO 3
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 3

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 4
<211> LENGTH: 951
<212> TYPE: DNA
<213> ORGANISM: Artificial Sequence
<220> FEATURE:
<223> OTHER INFORMATION: Synthetic polynucleotide

<400> SEQUENCE: 4
atggacagac ttacttcttc attcctgctc ctgattgtcc ctgcgtacgt cttgtccatc      60
acgtgccctc cccccatgtc cgtggaacac gcagacatct gggtcaagag ctacagcttg     120
tactccaggg agcggtacat tgtaactct ggtttcaagc gtaaagccgg cacgtccagc      180
ctgacggagt gcgtgttgaa caaggccacg aatgtcgccc actggacaac ccccagtctc     240
aaatgtatta gagagcccaa atcttgtgac aaaactcaca catgcccacc gtgcccagca     300
cctgaactcc tggggggacc gtcagtcttc ctcttccccc caaaacccaa ggacaccctc     360
atgatctccc ggacccctga ggtcacatgc gtggtggtgg acgtgagcca cgaagaccct     420
gaggtcaagt tcaactggta cgtggacggc gtggaggtgc ataatgccaa gacaaagccg     480
cgggaggagc agtacaacag cacgtaccgt gtggtcagcg tcctcaccgt cctgcaccag     540
gactggctga atggcaagga gtacaagtgc aaggtctcca acaaagccct cccagccccc     600

```
atcgagaaaa ccatctccaa agccaaaggg cagccccgag aaccacaggt gtacaccctg      660
cccccatccc gggatgagct gaccaagaac caggtcagcc tgacctgcct ggtcaaaggc      720
ttctatccca gcgacatcgc cgtggagtgg gagagcaatg ggcagccgga gaacaactac      780
aagaccacgc ctcccgtgct ggactccgac ggctccttct tcctctacag caagctcacc      840
gtggacaaga gcaggtggca gcaggggaac gtcttctcat gctccgtgat gcatgaggct      900
ctgcacaacc actacacgca gaagagcctc tccctgtctc cgggtaaata a              951
```

```
<210> SEQ ID NO 5
<211> LENGTH: 316
<212> TYPE: PRT
<213> ORGANISM: Artificial Sequence
<220> FEATURE:
<223> OTHER INFORMATION: Synthetic polypeptide

<400> SEQUENCE: 5
```

```
Met Asp Arg Leu Thr Ser Ser Phe Leu Leu Ile Val Pro Ala Tyr
1               5                   10                  15

Val Leu Ser Ile Thr Cys Pro Pro Met Ser Val Glu His Ala Asp
            20                  25                  30

Ile Trp Val Lys Ser Tyr Ser Leu Tyr Ser Arg Glu Arg Tyr Ile Cys
        35                  40                  45

Asn Ser Gly Phe Lys Arg Lys Ala Gly Thr Ser Ser Leu Thr Glu Cys
    50                  55                  60

Val Leu Asn Lys Ala Thr Asn Val Ala His Trp Thr Thr Pro Ser Leu
65                  70                  75                  80

Lys Cys Ile Arg Glu Pro Lys Ser Cys Asp Lys Thr His Thr Cys Pro
                85                  90                  95

Pro Cys Pro Ala Pro Glu Leu Leu Gly Gly Pro Ser Val Phe Leu Phe
            100                 105                 110

Pro Pro Lys Pro Lys Asp Thr Leu Met Ile Ser Arg Thr Pro Glu Val
        115                 120                 125

Thr Cys Val Val Val Asp Val Ser His Glu Asp Pro Glu Val Lys Phe
    130                 135                 140

Asn Trp Tyr Val Asp Gly Val Glu Val His Asn Ala Lys Thr Lys Pro
145                 150                 155                 160

Arg Glu Glu Gln Tyr Asn Ser Thr Tyr Arg Val Val Ser Val Leu Thr
                165                 170                 175

Val Leu His Gln Asp Trp Leu Asn Gly Lys Glu Tyr Lys Cys Lys Val
            180                 185                 190

Ser Asn Lys Ala Leu Pro Ala Pro Ile Glu Lys Thr Ile Ser Lys Ala
        195                 200                 205

Lys Gly Gln Pro Arg Glu Pro Gln Val Tyr Thr Leu Pro Pro Ser Arg
    210                 215                 220

Asp Glu Leu Thr Lys Asn Gln Val Ser Leu Thr Cys Leu Val Lys Gly
225                 230                 235                 240

Phe Tyr Pro Ser Asp Ile Ala Val Glu Trp Glu Ser Asn Gly Gln Pro
                245                 250                 255

Glu Asn Asn Tyr Lys Thr Thr Pro Pro Val Leu Asp Ser Asp Gly Ser
            260                 265                 270

Phe Phe Leu Tyr Ser Lys Leu Thr Val Asp Lys Ser Arg Trp Gln Gln
        275                 280                 285

Gly Asn Val Phe Ser Cys Ser Val Met His Glu Ala Leu His Asn His
    290                 295                 300
```

```
<210> SEQ ID NO 6
<211> LENGTH: 297
<212> TYPE: PRT
<213> ORGANISM: Artificial Sequence
<220> FEATURE:
<223> OTHER INFORMATION: Synthetic polypeptide

<400> SEQUENCE: 6

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295
```